United States Patent
Feger et al.

(10) Patent No.: US 7,005,416 B2
(45) Date of Patent: Feb. 28, 2006

(54) DALFOPRISTINE/QUINUPRISTINE COMBINATIONS WITH CEFPIROME

(75) Inventors: Céline Feger, Paris (FR); Philippe Moreillon, Lausanne (CH); Jacques Vouillamoz, Cully (CH)

(73) Assignee: Jones Pharma Incorporated, Bristol, TN (US)

( * ) Notice: Subject to any disclaimer, the term of this patent is extended or adjusted under 35 U.S.C. 154(b) by 372 days.

(21) Appl. No.: 09/920,810

(22) Filed: Aug. 3, 2001

(65) Prior Publication Data

US 2002/0037890 A1 Mar. 28, 2002

Related U.S. Application Data

(60) Provisional application No. 60/231,933, filed on Sep. 12, 2000.

(51) Int. Cl.
*A61K 38/00* (2006.01)
(52) U.S. Cl. .......................................................... 514/9
(58) Field of Classification Search ..................... 514/9
See application file for complete search history.

(56) References Cited

U.S. PATENT DOCUMENTS

| | | | | |
|---|---|---|---|---|
| 5,631,378 A | * | 5/1997 | Urawa et al. | |
| 5,686,441 A | * | 11/1997 | Maiti et al. | |
| 5,994,338 A | * | 11/1999 | Bounine et al. | |
| 6,187,746 B1 | * | 2/2001 | Conrath et al. | |
| 6,465,428 B1 | * | 10/2002 | Feger et al. | |

FOREIGN PATENT DOCUMENTS

FR  WO 98/22107  * 5/1998

\* cited by examiner

*Primary Examiner*—Michael Meller
(74) *Attorney, Agent, or Firm*—Jones Day

(57) ABSTRACT

A pharmaceutical composition comprising synergistically effective amounts of cefpirome and dalfopristine/quinupristine combination. A method of treating a patient comprising the administration of synergistically effective amounts of cefpirome and a dalfopristine/quinupristine combination. Kits comprising synergistically effective amounts of cefpirome and a dalfopristine/quinupristine combination are also disclosed.

15 Claims, 2 Drawing Sheets

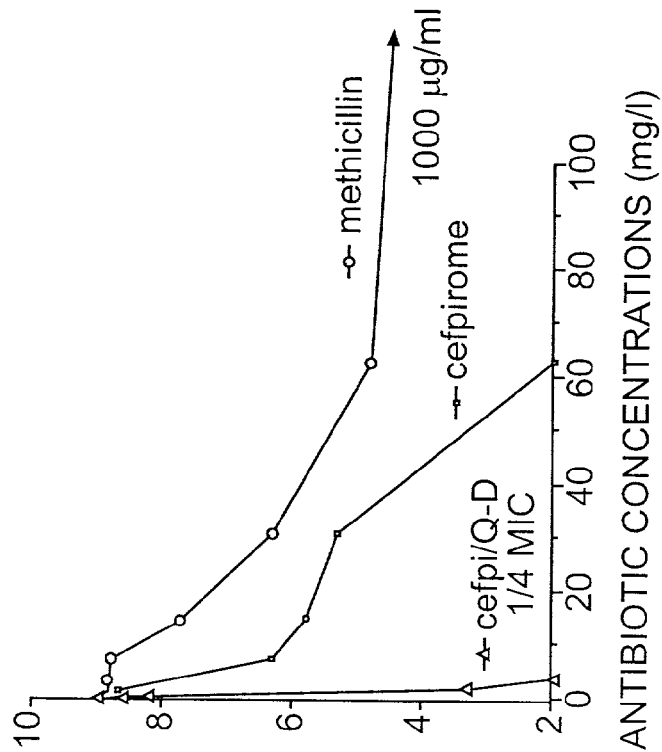
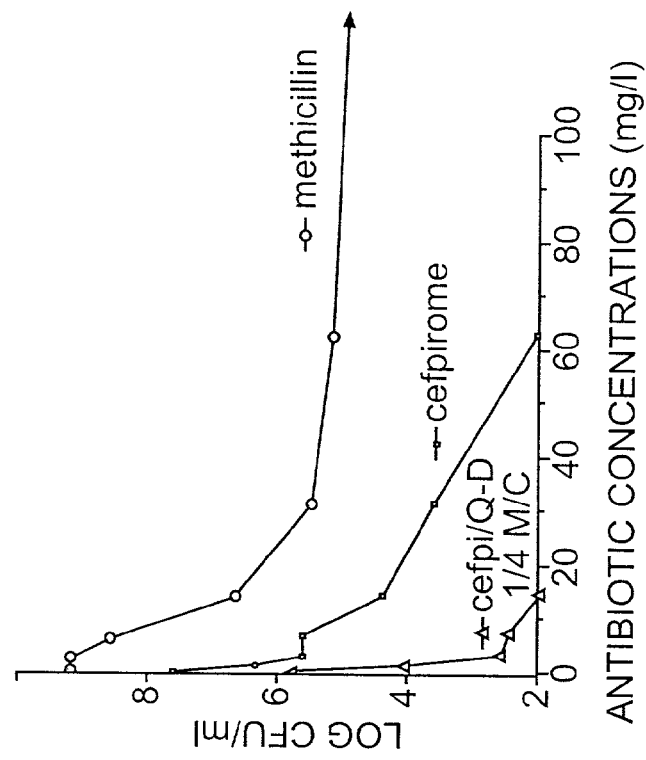

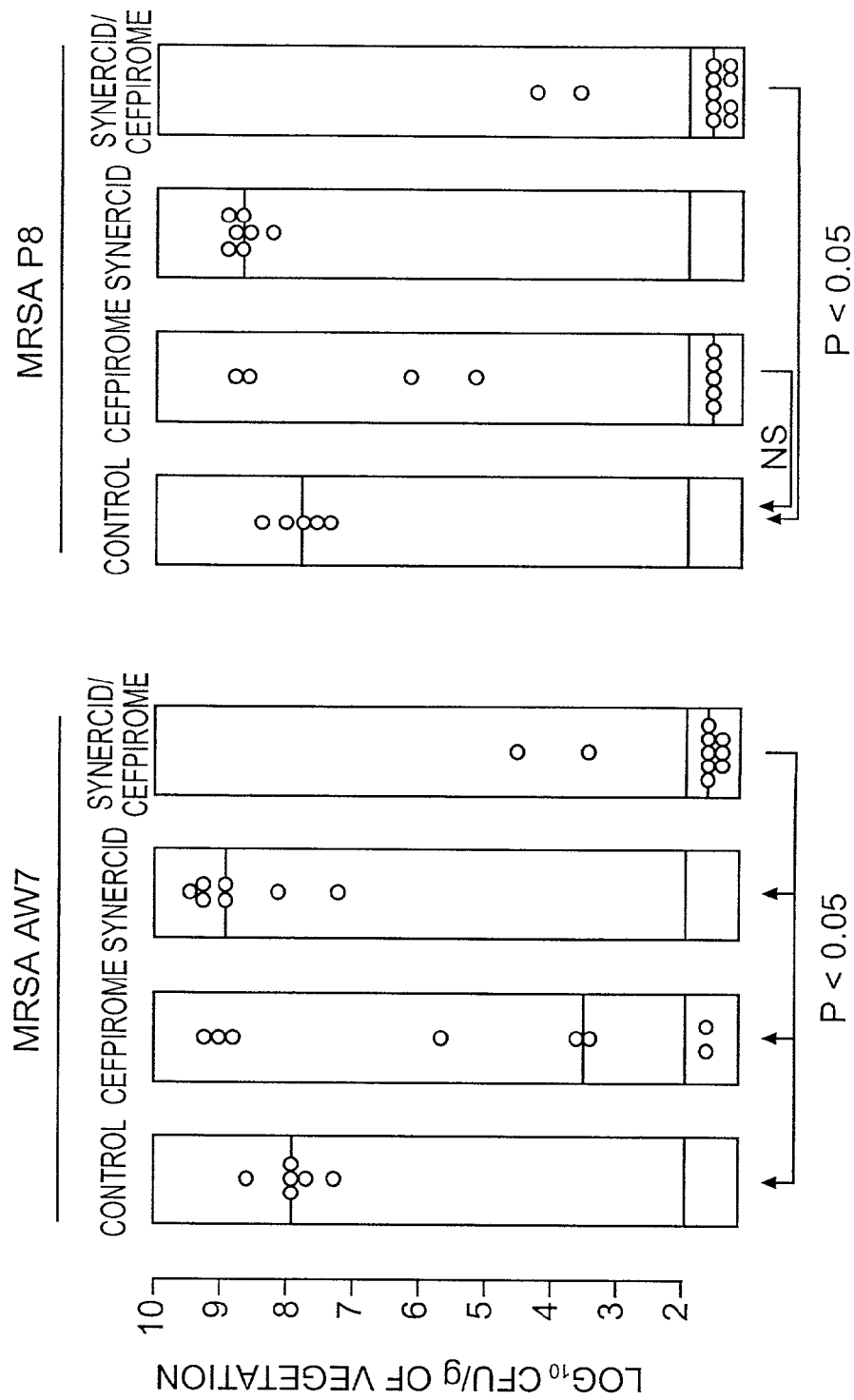

DALFOPRISTINE/QUINUPRISTINE COMBINATIONS WITH CEFPIROME

This application claims priority benefit of U.S. Provisional Application No. 60/231,933, filed Sep. 12, 2000.

The present invention relates to synergistic combinations of quinupristine/dalfopristine with cefpirome, both of which are bacteriostatic and bactericidal.

The present invention also relates to injectable and infusable pharmaceutical compositions for the parenteral administration of quinupristine and dalfopristine, combined with cefpirome. The present invention also relates to kits providing the active principles of the compositions according to the invention.

European Patent No. EP 248,703, the disclosure of which is incorporated by reference herein, describes derivatives of group B streptogramins of the formula:

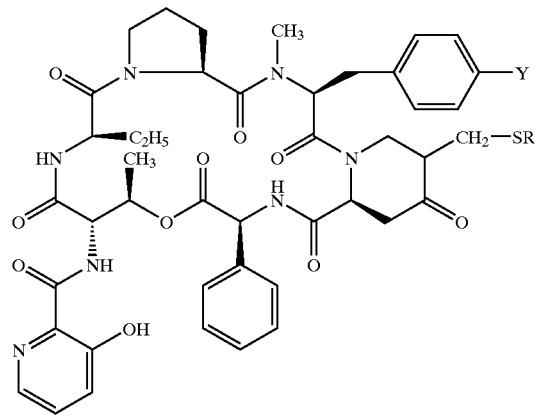

and their combinations with derivatives of group A streptogramins of the formula:

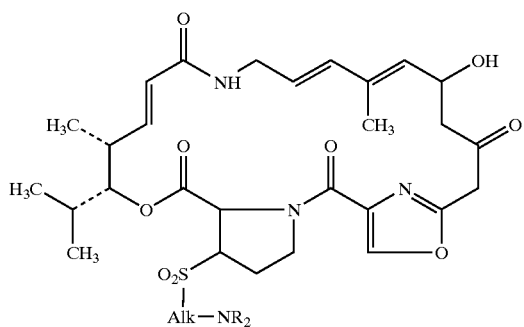

The derivatives of group A streptogramins are described in more detail in European Patent No. EP 191,662, the disclosure of which is incorporated by reference herein.

Quinupristine, which is a derivative of pristinamycin I (group B streptogramin), and dalfopristine, which is a derivative of pristinamycin II (group A streptogramin), are the constituents of Synercid®:

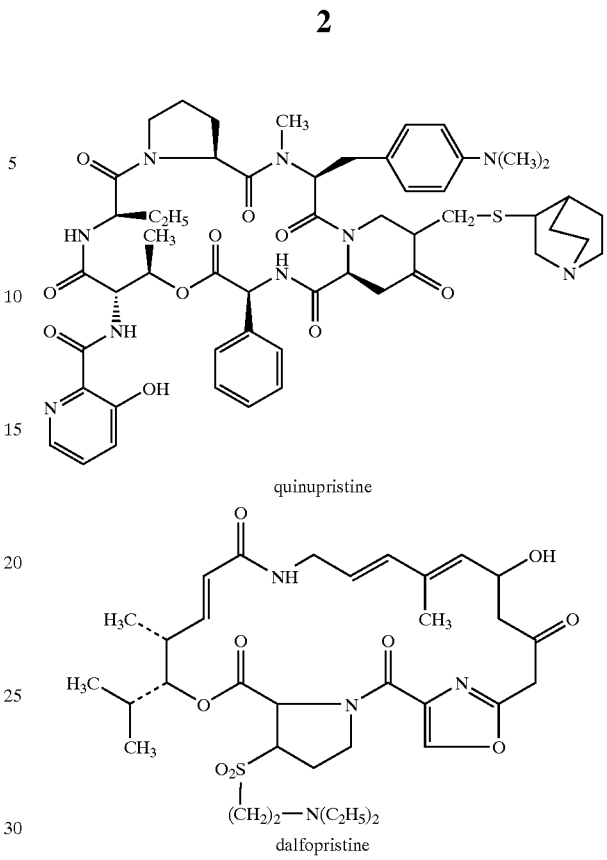

quinupristine dalfopristine

Synercid® (quinupristine/dalfopristine) is an injectable 30/70 combination that is effective on most gram-positive microorganisms such as, for example, meticillin-resistant *Staphylococcus aureus* (MRSA), Macrolide-Lincosamide-Streptogram in B-sensitive ($MLS_B$) *Staphylococcus aureus* and vancomycin-resistant *Enterococcus faecium* (VREF). Its antibacterial activity on, for example, vancomycin-resistant microorganisms, is cited in many publications, e.g., *The Annals of Pharmacotherapy*, 29, 1022–1026 (1995); *Microbial Drug Resistance*, 1, 223–234 (1995); and *Antimicrobial Agents Chemother.*, 39, 1419–1424 (1995), the disclosures of which are all incorporated by reference herein. However, Synercid® loses its bactericidal activity on staphylococci that are generally resistant to antibiotics of the Macrolide-Lincosamide-Streptogramin B group ($C-MLS_B$ resistant).

International Patent Application WO 98/22107, the disclosure of which is incorporated by reference herein, describes the preparation of stabilized pharmaceutical compositions comprising a quinupristine/dalfopristine combination, in the form of a salt obtained by adding methanesulfonic acid or hydrochloric acid in amounts that are at least stoichiometric, having a pH ranging from about 3.5 to about 5.

In the clinical environment, certain bacteria (such as $C-MLS_B$-resistant MRSA, for example) may compromise the effectiveness of the quinupristine/dalfopristine combination if appropriate concentrations of dalfopristine are not present at the site of infection. One of the means for resolving the problem has been the use of an increasing number of quinupristine/dalfopristine doses in a 24 hour period, or the use of a system of continuous infusion.

Cefpirome, having the chemical name (Z)-7-[2-(2-aminothiazol-4-yl)-2-methoxyiminoacetoamido]-3-(1-pyridinomethyl)-3-cephem-4-carboxylic acid sulfate [Martindale, 32$^{nd}$ edition, Kathleen Parfitt Ed.], is a β-lactam of the class of 4$^{th}$ generation cephalosporins that, compared with other products of this class, exhibits satisfactory activity against meticillin-resistant *Staphylococcus aureus* (MRSA) strains. It is conventionally administered parenterally by intravenous injection over 3 to 5 minutes, or by infusion over a period of 20 to 30 minutes, at cefpirome sulfate doses of 1 to 2 g per 12 hours depending on the severity of the infection. It is indicated in the treatment of urinary tract and respiratory tract infections and skin infections, and also in the treatment of septicemias and infections in immunodepressed individuals.

BRIEF DESCRIPTION OF THE DRAWINGS

FIG. 1 shows the activity of cefpirome monotherapy, quinupristine/dalfopristine monotherapy, and a combined cefpirome and quinupristine/dalfopristine combination therapy against two MRSA strains.

FIG. 2 shows the activity of cefpirome monotherapy, quinupristine/dalfopristine monotherapy, and a combined cefpirome and quinupristine/dalfopristine combination therapy on aortic endocarditis resulting from two MRSA strains.

It has now been found, in accordance with the present invention, that synergistic combinations of quinupristine/dalfopristine with cefpirome can provide a particular advantage in the treatment of infections that are difficult to treat or that put the life of the patient at risk, and which require rapid and effective bactericidal activity, as can be the case of combinations manifesting synergistic action against bacteria.

According to one embodiment, the present invention relates to a pharmaceutical composition comprising synergistically effective amounts of cefpirome and a dalfopristine/quinupristine combination.

According to another embodiment, the present invention relates to a method for treating a bacterial infection in a patient, the method comprising administering to a patient in need thereof synergistically effective amounts of cefpirome and a dalfopristine/quinupristine combination.

According to yet another embodiment, the present invention relates to a method for treating endocarditis comprising administering to a patient in need of such treatment synergistically effective amounts of cefpirome and a dalfopristine/quinupristine combination.

According to yet another embodiment, the present invention relates to a kit comprising synergistically effective amounts of cefpirome and of a dalfopristine/quinupristine combination.

The synergistic action of the combinations according to the invention provides a much higher potency, and can, for example, make it possible to decrease the quinupristine/dalfopristine or cefpirome concentration, or to increase the time between administration of the doses required to inhibit or eradicate a chosen bacterium (for example, with respect to multiresistant *staphylococci* such as, for example, the meticillin-resistant strains). The synergistic activity can also make it possible to treat infections on which each of the active principles, administered in monotherapy, would not have been effective.

Synercid® (quinupristine/dalfopristine) and cefpirome were tested separately in rats, on experimental endocarditis resulting from C-MLS$_B$-resistant MRSA strains.

Neither Synercid® nor cefpirome showed any effectiveness in vivo in monotherapy on the microorganisms studied. Conversely, the quinupristine/dalfopristine combination with cefpirome was effective in more than 90% of the rats treated.

The quinupristine/dalfopristine combination with cefpirome is particularly advantageous due to the fact that it may be a treatment of choice for patients requiring a simultaneous treatment for gram-positive and gram-negative microorganisms.

EXAMPLES

Materials and Methods

The studies carried out in vitro, and in vivo in animals, are described below.

The microorganisms tested were two clinical isolates of C-MLS$_B$-resistant MRSA: strains AW7 and P8, previously characterized in vitro, and in vivo in rat experimental endocarditis.

The study in vitro and the determination of the MICs (minimum inhibitory concentrations) was carried out using cultures on agar plates (Antimicrob. *Agents Chemother.*, 39, 1419–1424 (1995), the disclosure of which is incorporated by reference herein).

For the experimental endocarditis study, Wistar female rats weighing 200 g with aortic vegetation (produced according to the method described by Heraief et al., *Infect Immunol.*, 37,127–31 (1982), the disclosure of which is incorporated by reference herein) were infected with an inoculum of 10$^5$ CFU/ml of the organism to be tested, which corresponds to 10 times the minimum inoculum to produce endocarditis in at least 90% of the untreated controls (where CFU refers to colony forming units).

The treatment was started 12 hours after the bacterial infection, and was continued for 5 days. The antibiotics were administered by means of a permanent venous catheter with a programmable pump (Pump 44; Harvard Apparatus Inc.) according to the method described in *Antimicrobial Agents Chemother.*, 39, 1419–1424 (1995), the disclosure of which is incorporated by reference herein. The treatments simulated kinetics in humans, which were produced by intravenous administration of 7 mg/kg of quinupristine/dalfopristine every 12 hours, or by intravenous administration of 2 g of cefpirome every 12 hours. The relatively low dose of quinupristine/dalfopristine was chosen so as to demonstrate, where appropriate, a synergistic activity with the cefpirome.

Prior to the treatment experiments, the setting up of the simulation of the human kinetics of the quinupristine/dalfopristine combination with cefpirome in rats was performed on animals that were catheterized, but not infected. In these preliminary experiments, each point of the pharmacokinetics curve is the mean (±standard deviation) of the concentrations measured in 6 different rats. The concentrations of product in the serum were measured in a bioassay (using *Micrococcus luteus* for quinupristine/dalfopristine, and *Bacillus subtilis* ATCC 6633 for cefpirome).

The concentrations of quinupristine/dalfopristine in the serum of the rats were 5 mg/l, 1 hour after the start of treatment, and gradually decreased to undetectable concentrations after 6 hours. The concentrations of cefpirome were 160.6±19.7 mg/l, 5 minutes after the start of treatment, and gradually decreased to 2.2±1.4 mg/l after 12 hours. These values are in accordance with the therapeutic levels observed in humans for these active principles. In addition, during each treatment experiment, these concentrations were controlled in 3 rats taken randomly for each reference time of the pharmacokinetics.

The control rats were sacrificed at the start of the treatment and the treated rats were sacrificed 24 hours after the final antibiotic administration. The bacterial density in the vegetations was determined after dissecting the vegetations under sterile conditions, weighing, homogenizing in 1 ml of saline solution, and then diluting the solution (series of dilutions) before placing it onto plates for counting of the colonies. The number of colonies growing on the plates was determined after 48 hours of incubation at 35° C. The bacterial densities in the vegetations were expressed as $\log_{10}$ CFU/g of tissue. The minimum detection level was $\geq 2 \log_{10}$ CFU/g of vegetation.

The possibility of an emergence of resistance was also verified. The mean bacterial densities in the vegetations of the various groups were compared by the Kruskal-Wallis method, complemented with the Dunn method. The differences were considered to be significant when P was $\leq 0.05$.

RESULTS

The minimum inhibitory concentrations (MICs) of quinupristine/dalfopristine on the MRSA strains AW7 and P8 were 0.5 mg/l for each of the strains, and the MICs for cefpirome were, respectively, 4 mg/l on AW7 and 2 mg/l on P8.

Bacterial populations of the MRSA strains Ab 7 and P8 can grow on plates containing up to 60 mg/l of cefpirome. It was observed, after addition to the plates of subinhibitory concentrations (¼MIC—noneffective concentration) of the dalfopristine/quinupristine combination, that the strain AW7 did not grow on plates containing concentrations $\geq 5$ mg/l of cefpirome, and that the strain P8 did not grow on plates containing concentrations $\geq 15$ mg/l of cefpirome.

FIG. 1 illustrates this synergistic action.

The in vivo study in rat experimental endocarditis also made it possible to demonstrate synergistic activity.

FIG. 2 shows that neither quinupristine/dalfopristine, nor cefpirome, in monotherapy were significantly effective on the aortic endocarditis resulting from the MRSA strains AW7 and P8 (P>0.05). By contrast, as also shown in FIG. 2, the combination of quinupristine/dalfopristine with cefpirome was shown to be significantly effective (P<0.05) on each of the strains ($\log_{10}$ CFU/g of vegetation $\leq 2$ in more than 80% of the cases). This is also shown in the tables below.

| | MRSA AW7 | | | |
|---|---|---|---|---|
| | Control | Cefpirome | Synercid ® | Synercid/ cefpirome |
| $\log_{10}$ CFU/g of vegetation | from 7.2 to 8.6 in 100% of the cases | >8.7 in 38% of the cases; approximately 3.5 in 25% of the cases; and $\leq 2$ in 25% of the cases | >7.2 in 100% of the cases of which $\geq 9$ in 70% of the cases | $\leq 2$ in 80% of the cases, and 3.5 to 4.6 in 20% of the cases |

| | MRSA P8 | | | |
|---|---|---|---|---|
| | Control | Cefpirome | Synercid ® | Synercid ®/ cefpirome |
| $\log_{10}$ CFU/g of vegetation | >7.5 in 100% of the cases | 8.7 to 9 in 22% of the cases; 5.4 to 6.3 in 22% of the cases; and $\leq 2$ (not significant) in 55% of the cases | >8.4 in 100% of the cases | $\leq 2$ in 80% of the cases, and 3.6 to 4.4 in 18% of the cases |

As a result, treatment with such a combination makes it possible to attain an effectiveness which was not obtained in monotherapy, while allowing the use of lower doses of the products combined or the choice of longer intervals between administrations. The treatment also permits a greater bacteriostatic and bactericidal effectiveness than that which was attained in monotherapy. In particular, in the case of severe infections (such as, for example, endocarditis), the synergistic activity of the combination makes it possible to use the cefpirome at usual doses, whereas in the absence of the synergism-producing combination, it would have been necessary, in order to obtain effectiveness, to increase the doses to such a level that cefpirome could not have been used.

The doses of the Synercid® quinupristine/dalfopristine combination administered to patients may range from about 5 to about 15 mg/kg every 12 hours. According to another embodiment, the amount may range from about 5 to about 7.5 mg/kg every 8 hours.

The dose of cefpirome conventionally administered to patients may range from about 2 to about 4 g per day in two infusions or two direct intravenous injections, or about 1 to about 2 g every 12 hours, depending on the severity of the infection.

In the combinations above, the quinupristine/dalfopristine combinations with cefpirome can be advantageously used for treating patients as a continuous injection or in several administrations. The doses chosen depend on the bacterial infection to be treated and the synergistic effect desired.

When synergism makes it possible, due to the combination, to obtain an effect on microorganisms which could not have been treated in monotherapy with one or other of the active principles, the doses combined can be chosen within the range of doses conventionally used in monotherapy or, where appropriate, can be lower doses depending on the nature of the infection. For example, daily doses of quinupristine/dalfopristine may range from about 15 to about 30 or about 15 to about 60 mg/kg, or may range from about 10 to about 30 or about 10 to about 60 mg/kg, in fractionated doses or as a continuous injection, and daily doses of cefpirome ranging from about 2 to about 4 g in two infusions or in two direct intravenous injections.

The synergistic activity of the compositions according to the invention permit the treatment of bacterial infections at lower doses of quinupristine/dalfopristine and/or cefpirome, thus minimizing the risks of side effects (for example, in the case of microorganisms showing less resistance). As a result of this synergistic activity, the combined doses of quinupristine/dalfopristine and cefpirome can be chosen from a smaller range relative to the maximum usable dose in monotherapy. For example, doses of quinupristine/dalfopristine can range from 10 to 22.5 or from 10 to 30 mg/kg maximum in fractionated doses or as a continuous injection. Cefpirome may be administered in an amount ranging from 2 to 4 g in two infusions or in two direct intravenous injections.

As can be appreciated by those of ordinary skill in the art, the compositions according to the invention can be provided in several types of administration, for example, simultaneous coadministration, successive administration at delayed times, or administration via multilumen (multichannel) catheters.

For treatment, the quinupristine/dalfopristine formulations may be in liquid, lyophilized, or frozen form. The lyophilized compositions can be taken up, at the time of use, in water for injection (WFI), or in any other compatible injectable medium, for example a glucose medium (aqueous solution of 5% glucose for example), or, without any limitation being implied, in dextran solutions, polyvinylpyrrolidone solutions, or polysorbate 80 solutions. According to one embodiment of the invention, the formulations are redissolved by intermediate passage via a concentrated solution (for example, 50 to 250 mg/ml, or approximately 100 mg/ml), hereafter called "concentrate." This solution may be diluted at the time of use in a medium for injection, as described above, for administration in the form of infusion. It is also possible to take the lyophilizate up in WFI, and then dilute the concentrate thus obtained in the chosen injection medium.

The pharmaceutical compositions can be frozen from the solutions initially prepared (5 to 250 mg/ml), or from prediluted solutions (for the preparation of frozen bags, for example). They may be thawed at the time of use and then diluted, if necessary. The solutions provided in liquid form may contain 5 to 250 mg/ml of active ingredient. They may be diluted at the time of use to concentrations ranging from 0.5 to 10 mg/ml.

According to one aspect of the invention, the quinupristine/dalfopristine formulations, which are optionally in the form of a concentrated solution or a diluted solution, can be combined, for coadministration, with a solution of cefpirome at the time of injection. The combination can be provided in a number of types of containers, for example, in the form of two infusion bags, one containing the quinupristine/dalfopristine in its injection medium and the other containing the solution of cefpirome, or by using two syringes, one containing quinupristine/dalfopristine and the other containing the solution of cefpirome. Alternatively, the combination can be provided with one of the active principles in an infusion bag and the other in a syringe.

It is understood that kits for the formulation of quinupristine/dalfopristine and cefpirome also fall within the context of the present invention.

Kits of any form can be suitable. For example, the kits can be provided in the form of twin-bottle kits, in the form of infusion bags containing the active principles, and in the form of an infusion bag containing one of the active principles and a bottle or vial containing the other active principle. Alternatively, the kit can be provided in the form of one or more bottles comprising one of the active principles (for example, comprising the quinupristine/dalfopristine lyophilizate), and a bottle or vial containing the other active principle. Devices such as a double-compartment syringe may also be included in the kits according to the invention.

It is understood that the present invention can also apply to other derivatives of pristinamycin, such as, for example, the derivatives described in European Patent Nos. EP 133,097, EP 135,410, EP 191,662, and EP 248,703, and International Patent Application Nos. WO 99/43699 and WO 99/05165, the disclosures of which are all incorporated by reference herein.

What is claimed is:

1. A pharmaceutical composition comprising synergistically effective amounts of:
   (A) cefpirome, and
   (B) a dalfopristine/quinupristine combination.

2. A pharmaceutical composition according to claim 1, wherein quinupristine and dalfopristine are present in a ratio of approximately 30:70.

3. A pharmaceutical composition according to claim 1, wherein said dalfopristine/quinupristine combination is in a liquid, lyophilized, or frozen form.

4. A method for treating a bacterial infection in a patient, said method comprising administering to a patient in need there of synergistically effective amounts of:
   (A) cefpirome, and
   (B) a dalfopristine/quinupristine combination.

5. A method for treating a bacterial infection in a patient according to claim 4, wherein said cefpirome and said dalfopristine/quinupristine combination are administered simultaneously or sequentially.

6. A method for treating a bacterial infection in a patient according to claim 4, wherein said cefpirome and said dalfopristine/quinupristine combination are administered through a multilumen catheter.

7. A method for treating a bacterial infection in a patient according to claim 4, wherein said cefpirome and said dalfopristine/quinupristine combination are administered in the form of two infusion bags, one containing the cefpirome and the other containing the dalfopristine/quinupristine combination.

8. A method for treating a bacterial infection in a patient according to claim 4, wherein said cefpirome and said dalfopristine/quinupristine combination are administered in the form of two syringes, one containing the cefpirome and the other containing the dalfopristine/quinupristine combination.

9. A method for treating a bacterial infection in a patient according to claim 4, wherein said cefpirome and said dalfopristine/quinupristine combination are administered in the form of an infusion bag and a syringe, with one containing the cefpirome and the other containing the dalfopristine/quinupristine combination.

10. A method for treating a bacterial infection in a patient according to claim 4, wherein said patient is in need of treatment for infections caused by both gram-positive and gram-negative microorganisms.

11. A method for treating a bacterial infection according to claim 4, wherein the dalfopristine/quinupristine combination is administered to said patient in an amount ranging from about 5 to about 60 mg/kg/day and the cefpirome is administered in an amount ranging from about 2 to about 4 g/day.

12. A method for treating a bacterial infection according to claim 4, wherein the dalfopristine/quinupristine combination is administered to said patient in an amount ranging from about 10 to about 30 mg/kg/day and the cefpirome is administered in an amount ranging from about 2 to about 4 g/day.

13. A method for treating a bacterial infection according to claim 11, wherein the cefpirome is administered in two infusions, two direct intravenous injections, or one infusion and one direct intravenous injection.

14. A method for treating a bacterial infection according to claim 12, wherein the cefpirome is administered in two infusions, two direct intravenous injections, or one infusion and one direct intravenous injection.

15. A method for treating endocarditis, said method comprising administering to a patient in need of such treatment synergistically effective amounts of cefpirome and a dalfopristine/quinupristine combination.

* * * * *